(12) United States Patent
Jackowski et al.

US007014854B2

(10) Patent No.: US 7,014,854 B2
(45) Date of Patent: Mar. 21, 2006

(54) METHOD FOR RETARDING OR PRECLUDING ALZHEIMER'S DEMENTIA

(75) Inventors: George Jackowski, Kettleby (CA); Shirley Furesz, Cambridge (CA)

(73) Assignee: Syn X Pharma, Inc., Ontario (CA)

( * ) Notice: Subject to any disclaimer, the term of this patent is extended or adjusted under 35 U.S.C. 154(b) by 98 days.

(21) Appl. No.: 10/334,701

(22) Filed: Dec. 30, 2002

(65) Prior Publication Data
US 2003/0152570 A1 Aug. 14, 2003

Related U.S. Application Data

(63) Continuation-in-part of application No. 09/859,559, filed on May 16, 2001, now abandoned.

(51) Int. Cl.
*A61K 39/00* (2006.01)

(52) U.S. Cl. .................................................. 424/140.1
(58) Field of Classification Search ............. 424/140.1, 424/9.1, 142.1; 435/7.92
See application file for complete search history.

(56) References Cited

U.S. PATENT DOCUMENTS

| | | | |
|---|---|---|---|
| 4,627,915 A | 12/1986 | Kurodo et al. | |
| 5,004,697 A | 4/1991 | Pardridge | |
| 5,098,372 A | 3/1992 | Jonsson | 604/5 |
| 5,627,047 A | 5/1997 | Brenner et al. | |
| 5,723,301 A | 3/1998 | Burke et al. | |
| 5,935,927 A | 8/1999 | Vitek et al. | |
| 6,043,224 A | 3/2000 | Lee et al. | |
| 6,187,756 B1 | 2/2001 | Lee et al. | |

FOREIGN PATENT DOCUMENTS

| | | |
|---|---|---|
| WO | WO 93/10459 | 5/1993 |
| WO | WO 02/088706 | 11/2002 |

OTHER PUBLICATIONS

Dermer, G. Bio/Technology, 12 :320, 1994.*
Pardridge, W.M., Journal of Neurochem. 70: 1781-1792, 1998.*
Sunaga, et al., "Glyceraldehyde-3-phosphate dehydrogenase is over-expressed during apoptotic death of neuronal cultures and is recognized by a monoclonal antibody against amyloid plaques from Alzheimer's brain", Neuroscience Letters (1995) vol. 200, No. 2, pp. 133-136.
Borden, "Structure/Function in Neuroprotection and Apoptosis", Annals of Neurology (1998) vol. 44, No. 3, pp. 565-571.
Terryberry, et al., "Autoantibodies in Neurodegenerative Diseases: Antigen-Specific Frequencies and Intrathecal Analysis", Neurobiology of Aging (1998), vol. 19, No. 3, pp. 205-216.

Albrechtsen, et al., Enzyme-linked immunosorbent assay for the human glial fibrillary acidic protein using a mouse monoclonal antibody, (1985) vol. 11, No. 102, p 277.
Patent Abstracts of Japan, "Method and Device for Processing Blood By Plasma Exchange" vol. 1998, No. 8.
Hensley et al., A Model for β-amyloid aggregation and neurotoxicity based on free radical generation by the peptide: Relevance to Alzheimer disease, Proc. Natl. Acad. Sci., (1994) 91, pp. 3270-3274.
Sunaga et al., "Glyceraldehyde-3-phosphate dehydrogenase is over-expressed during apoptotic death of neuronal cultures and is recognized by a monoclonal antibody against amyloid plaquest from alzheimer's brain", Neuroscience Letters, (1995) 100, pp. 133-136.
Popovic et al., "Importance of immunological and inflammatroy processes in the pathogenesis and therapy of alzheimer's disease", Int. J. Neurosci., (1998) 95, 3-4, pp. 203-236.
Joachim CL, et al., "Clinically diagnosed Alzheimer's disease: autopsy results in 150 cases", (1988) Ann Neurol 24 (1): 50-6 (abstract only).
Mc Swigan JD, et al., "An analysis of glial fibrillary acidic protein in Alzheimer's disease", (1983) Fed. Proc. 42 (7), abstract p. 1475.
Selkoe DJ, "Clearing the brain's amyloid cob webs", (2001) Neuron 32: pp. 177-180.
Mecocci, et al., "Serum Autoantibodies against Glial Fibrillary Acidic Protein in Brain Aging and Senile Dementias", Brain, Behavior, and Immunity (1992) 6: pp. 286-292.
Summary of I'ponna, et al., *Mental Disorders in Later Life* (1956), pp. 289-331.
Ishida, et al., "Identification and characterization of an anti-glial fibrillary acidic protein antibody with a unique specificity in a demented patient with an autoimmune disorder", J. Of Neurological Sciences (1997) 151: pp. 41-48.

(Continued)

*Primary Examiner*—Janet L. Andres
*Assistant Examiner*—Gyan Chandra
(74) *Attorney, Agent, or Firm*—McHale & Slavin, P.A.

(57) ABSTRACT

A method for treating a condition related to the development of Alzheimer's disease (AD) is disclosed. The method involves the removal of circulating autoantibodies of a biochemical marker or markers, specifically human glial fibrillary acidic protein (GFAP) and glyceraldehyde-3-phosphate dehydrogenase (GAPDH), from the sera of a patient in an amount effective to reduce or eliminate phagocytosis of astrocytic cells. The invention further includes a process of immune system modulation effective for autoantibody removal.

1 Claim, 3 Drawing Sheets

OTHER PUBLICATIONS

Lopez et al., "Serum auto-antibodies in Alzheimer's disease", Acta Neurol Scand (1991) 84: pp. 441-444.

Tanaka, et al., "Enzyme-linked immunosorbent assay for human autoantibody to glial fibrillary acidic protein: higher titer of the antibody is detected in serum of patients with Alzheimer's disease", Acta Neurol. Scand (1989) 80: pp. 554-560.

Odabasi, et al., "Polyhydroxyethylmethacrylate-based magnetic DNA-affinity beads for anti-DNA antibody removal from systemic lupus erythematosus patient plasma", Journal of Chromatography B (2001), 760(1): pp. 137-148.

Graninger et al., "Immunoadsorption Therapy (Therasorb) in Patients with Severe Lupus Erythematosus", Acta Medica Austriaca-Heft 1 (2002) 29(1): pp. 26-29.

Suzuki, "The Role of Immunoadsorption Using Dextran-Sulfate Cellulose Columns in the Treatment of Systemic Lupus Erythematosus", Therapeutic Apheresis (2000) 4(3): pp. 239-243.

* cited by examiner

Western Blot of Brain Tissue Extracts

2D gels of Brain Extracts

Alzheimer's Brain Extract

Normal Brain Extract

METHOD FOR RETARDING OR PRECLUDING ALZHEIMER'S DEMENTIA

REFERENCE TO RELATED APPLICATIONS

This application is a continuation-in-part of Ser. No. 09/859,559, filed on May 16, 2001 now abandoned, the entire contents of which is incorporated herein by reference.

FIELD OF THE INVENTION

The present invention relates to a method useful in treating a condition related to the development of Alzheimer's disease (AD). The invention particularly relates to a process retarding or precluding Alzheimer's dementia by reducing or eliminating the concentration of at least one auto-antibody whose presence has been shown to initiate phagocytosis of astrocytic cells, thereby leading to Alzheimer's disease.

BACKGROUND OF THE INVENTION

Alzheimer's disease, also referred to as Alzheimer's dementia or AD is a progressive neurodegenerative disorder that causes memory loss and serious mental deterioration. Diagnosticians have long sought a means to definitively identify AD during the lifetime of demented patients, as opposed to histopathological examination of brain tissue, which is the only present means available for rendering an ultimate diagnosis of AD. AD is the most common form of dementia, accounting for more than half of all dementias and affecting as many as 4 million Americans and nearly 15 million people worldwide. Dementia may start with slight memory loss and confusion, but advances with time reaching severe impairment of intellectual and social abilities. At age 65, the community prevalence of AD is between 1–2%. By age 75, the figure rises to 7%, and by age 85 it is 18%. The prevalence of dementia in all individuals over age 65 is 8%. Of those residing in institutions, the prevalence is about 50%, at any age.

The social impact of this disease is enormous, caused by the burden placed on caregivers, particularly in the latter stages of the disease. The substantial economic costs are largely related to supportive care and institutional admission. The rapidly increasing proportion of elderly people in society means that the number of individuals affected with AD will grow dramatically, therefore finding an early accurate diagnosis and a cure for AD is becoming an issue of major importance world wide.

When an individual is suspected of AD, several recommended tests are performed:(1) Mini Mental State Examination (MMSE)—an office-based psychometric test in the form of a Functional Assessment Questionnaire (FAQ) to examine the scale for functional autonomy, (2) Laboratory tests—complete blood count, measurement of thyroid stimulating hormone, serum electrolytes, serum calcium and serum glucose levels, (3) Neuroimaging—most commonly used is computed tomography (CT) which has a role in detecting certain causes of dementia such as vascular dementia (VaD), tumor, normal pressure hydrocephalus or subdural hematoma. However, neuroimaging is less effective in distinguishing AD or other cortical dementias from normal aging. In primary care settings, some suggest that CT could be limited to atypical cases, but others recommend routine scanning. Magnetic resonance imaging (MRI) currently offers no advantage over CT in most cases of dementia.

While Alzheimer's is the most common form of dementia, accounting for at least 60% of cases, diagnostic procedures for determining the exact cause of dementia, among more than 80 different species, is difficult at best.

In comparison to other disease areas, the field of dementia raises questions concerning the value of diagnosis, since there is currently no cure or effective therapy available. In dementia, as in all other branches of medicine, the certainty of a diagnosis has an important impact on the management of the patient. While AD cannot be cured at present time, there is symptomatic treatment available and the first drugs (acetylcholinesterase inhibitors) for the temporary improvement of cognition and behavior are now licensed by the U.S. Food and Drug Administration. Other drugs are at different stages of clinical trials:(1) Drugs to prevent decline in AD—DESFERRIOXAMINE, ALCAR, anti-inflammatory drugs, antioxidants, estrogen, (2) Neurotrophic Factors: NGF, (3) Vaccine:the recent most exciting report by Schenk et al. (Nature 1999;400:173–7) raises the hope of a vaccine for AD. Unfortunately, a percentage of patients cannot tolerate the pharmaceutical agents currently made available due to allergic reactions, drug interactions, genetic inability to properly metabolize the agent, or the like, and therefore are unable to utilize the medicinal advantages of these agents. In addition, the pharmaceutical agents themselves have limited therapeutic value. After a length of time, the agent no longer is able to function as intended due to the body's tolerance, resulting in the buildup of autoantibodies. In this case, alternate therapy to control the level of autoantibodies circulating in the body by periodic removal may increase the length of time of an agent's medicinal value.

The specificity of the various therapies thus require sophisticated diagnostic methodologies, having a high degree of sensitivity for AD, in order to insure their success.

Currently there are a multitude of tests available which aid in the diagnosis of AD. However, the only true existing diagnosis is made by pathologic examination of postmortem brain tissue in conjunction with a clinical history of dementia. This diagnosis is based on the presence in brain tissue of neurofibrillary tangles and of neuritic (senile) plaques, which have been correlated with clinical dementia. Neuritic plaques are made up of a normally harmless protein called amyloid-beta. Before neurons begin to die and symptoms develop, plaque deposits form between neurons early on in the disease process. The neurofibrillary tangles are interneuronal aggregates composed of normal and paired helical filaments and presumably consist of several different proteins. The internal support structure for brain neurons depends on the normal functioning of a protein called tau. In Alzheimer's disease, threads of tau protein undergo alterations that cause them to become twisted. The neurohistopathologic identification and counting of neuritic plaques and neurofibrillary tangles requires staining and microscopic examination of several brain sections. However, the results of this methodology can widely vary and is time-consuming and labor-intensive.

Given the ability of both current and prospective pharmacological therapies to forestall and/or reverse the onset and/or progress of Alzheimer's dementia, it behooves us to promulgate interim methodologies to delay the seemingly irreversible loss of cognitive function.

Various biochemical markers for AD are known and analytical techniques for the determination of such markers have been described in the art. As used herein the term "marker" "biochemical marker" or "marker protein" refers to any enzyme, protein, polypeptide, peptide, isomeric form thereof, immunologically detectable fragments thereof, or other molecule that is released from the brain during the course of AD pathogenesis. Such markers may include, but are not limited to, any unique proteins or isoforms thereof that are particularly associated with the brain.

The markers particularly targeted according to the method of the invention are glial fibrillary acidic protein (GFAP) and glyceraldehyde-3-phosphate dehydrogenase (GAPDH).

Glial fibrillary acidic protein is an intermediate filament protein found almost exclusively in astrocytes which, in adults, control the level of GFAP expression. Astrocytes are a major type of glial cell which perform a variety of structural and metabolic functions, such as processing neurotransmitters, controlling extracellular ion levels, regulating the direction and amount of nerve growth, maintaining the blood-brain barrier, and participating in immune reactions. As astrocytes transform from a resting state into a process-bearing reactive state during events such as aging, GFAP expression is up-regulated. Since levels have been found to increase in the brain tissue and cerebrospinal fluid in patients suffering from AD, it has been suggested that reactive astrocytes may contribute to the neuropathology of AD (Wallin et al. Dementia, 7, 267 (1996)). In the AD brain, the loss of synapses is associated with an increase in the number of GFAP-positive astrocytes. In addition, this loss of synapses appears to be related to the extent of reactive astrogliosis (Brun et al., Neurodegeneration, 4, 171 (1995)). GFAP is a major component of the gliotic scars which result from gliosis, and which may interfere with subsequent reinnervation.

Glyceraldehyde-3-phosphate dehydrogenase is ubiquitous in the cell, with the major fraction in the cytoplasm associated with cytoskeletal proteins and membranes, and small amounts in the nucleus (van Tuinen et al., J. Histochem. Cytochem., 35 (1987)). Its size has been characterized in the prior art as between 35,000 to 38,000 Daltons. As a monomer, GAPDH promotes tubulin polymerization, the major constituent of microtubules (Durrieu et al., Arch. Biochem. Biophys., 252, 32 (1987)). GAPDH has many enzymatic and binding activities including forming complexes with the C-terminal region of the amyloid precursor protein (Schulze et al., J. Neurochem., 60 (1993)). The disruption in binding of GAPDH to cytoskeletal elements such as tubulin can result in the alteration of neuronal morphology, function, and survival. Its involvement in the neurodegeneration during the development of AD has been hypothesized due to its link to amyloid plaques (Sunaga et al., Neurosci. Lett., 200, 2 (1995)).

The present inventors have theorized that when autoantibodies to GFAP and/or GAPDH proliferate in the bloodstream and cross the blood-brain barrier, they couple with GFAP positive cells, particularly astrocytic cells. In the presence of these autoantibodies, e.g. anti-GFAP antibodies, the macrophages become clumped around the astrocytes, thereby initiating the phagocytosis process. If it could be demonstrated that the concentration of these autoantibodies are a controlling factor in the initiation of astrocytosis, then it would be possible to alter the course of disease progression by modifying anti-GFAP or the like autoantibodies associated with biochemical markers for AD in the circulating sera, thus providing physicians with an additional method for possibly circumventing or delaying loss of cognition at an early stage in the pathogenesis of this disease.

Certain types of treatment devices are known to be useful for the removal of biological markers. Removal of these markers is also known to be a valuable tool for reducing the manifestations of disease progression.

What is lacking in the art is a method effective for altering the course of disease initiation/progression in living Alzheimer's dementia patients alone, or in conjunction with, the use of pharmaceutical agents.

DESCRIPTION OF THE PRIOR ART

Generally, most scientific papers tend to focus on the peptide, β-amyloid, since it is postulated to be a major determinant of AD. This is supported by the observation that certain forms of familial AD mutations result in the over production of β-amyloid, particularly the longer form (1–42) which aggregates more readily than the shorter form. Hensley et al. (Proc. Natl. Acad. Sci., (1994), 91, pp3270–3274) examine the neurotoxicity based on free radical generation by the peptide β-amyloid in its aggregation state. Several synthetic fragments of the peptide are tested for resulting neurotoxicity. Based on the fact that oxygen seems to be a requirement for radical generation and glutamate synthetase and creatine kinase enzymes are oxidation-sensitive biomarkers, the inactivation of these enzymes are utilized as indicators of active attack on biological molecules by these fragmented β-amyloid aggregates.

In U.S. Pat. No. 5,004,697, Pardridge describes the use of modified antibodies for treatment and diagnosis of neurological diseases. A diagnostic composition is claimed involving an antibody capable of binding to antigens present in GFAP protein or an antibody to an Alzheimer's disease amyloid peptide. Delivery of these antibodies across the blood-brain barrier (BBB) is essential to the Pardridge invention in order to achieve diagnostic and/or therapeutic efficacy. Pardridge therefore requires modification of the antibodies by a process of cationization. There is no disclosure regarding the removal of circulating autoantibodies as a treatment method.

In U.S. Pat. No. 5,627,047, Brenner et al teaches astroctye-specific transcription of human genes. GFAP is acknowledged in the evaluation of AD, specifically the gene which encodes GFAP, however the patent is silent regarding autoantibodies to GFAP.

U.S. Pat. No. 6,187,756, a divisional of U.S. Pat. No. 6,043,224, issued to Lee et al. describes a method of alleviating the negative effects of a neurological disorder or neurodegenerative disease. The manner of alleviation is by administration of an antagonist of a β-adrenergic receptor coupled to cAMP or the administration of a protein kinase A or C signaling agent, for example. The importance of GFAP is only seen as it relates to cAMP; GFAP expression in astrocytes is increased by elevation in cAMP levels. Neither GFAP nor its autoantibody are recognized as having any significance in the treatment of AD.

U.S. Pat. No. 5,723,301 issued to Burke et al. teaches a method to screen compounds that affect GAPDH binding to polyglutamine. The role of GAPDH in neuronal death as a result of brain injury is described. Although a link of GAPDH to Alzheimer's disease is disclosed, the interest lies only in polyglutamine regions. Neither GAPDH nor its autoantibody are recognized as a target useful for direct intervention in the disease.

Many scientists have explored the significance of myelin basic protein, neuron specific enolase, and S100 autoantibodies in AD. As far as GFAP, there are conflicting results and opinions regarding the significance of serum autoantibodies against this protein. Although it has been suggested that the presence of anti-GFAP autoantibodies is related to Alzheimer's dementia, it is only as a secondary response. Generally, when GAPDH is utilized in Alzheimer's work, it is as a housekeeping gene or mRNA probe for other proteins of interest in the disease. Nothing in the prior art would suggest that a reduction in the amount of circulating autoantibodies to GFAP and GAPDH could have a beneficial effect in retarding the manifestations of Alzheimer's dementia. In addition, it has not been previously suggested to remove the circulating autoantibodies associated with these proteins to alleviate symptoms of the disease state.

SUMMARY OF THE INVENTION

The present invention is directed toward a process and a device which is useful for altering the progression of astrocyte phagocytosis, whereby the progression or development of Alzheimer's dementia may be altered or even eliminated. Although not wishing to be bound to any particular theory or hypothesis, the instant inventors have recognized what appears to be a causal relationship between the presence of certain autoantibodies, particularly those which bind to GAPDH and GFAP in circulating sera, and the progressive loss of cognitive ability associated with AD. it is theorized that reduction of these autoantibodies within the circulating sera, as a sole therapeutic modality or alternatively in conjunction with pharmacologic therapeutic agents, e.g. acetylcholinesterase inhibitors, may be effective in altering the development and/or progression of the disease, including but not limited to retardation of disease progression and/or increase of the period of efficacy of adjunct therapy. To this end, the instant inventors have demonstrated a causal relationship between the presence of autoantibodies to GFAP and the initiation of phagocytosis of astrocyte cells.

While it has not yet been conclusively demonstrated that a process for reduction of GFAP autoantibodies in circulating sera will modulate the development of Alzheimer's disease, it has nevertheless been shown that removal of such autoantibodies from circulating sera does, in fact, eliminate the initiation of phagocytosis of astrocytes.

While not wishing to be bound to a particular theory or mode of operation, it is believed that provision of a device to facilitate antigen-antibody interaction by creating an interfacial area containing a population of immobilized proteins which bind to the targeted autoantibodies; will result in a reduction in said phagocytosis, coupled with a concomitant reduction in the formation of plaques associated with Alzheimer's. These immobilized proteins, which function as a ligand, may be attached in various ways to a base, e.g. polystyrene, silicone, silica, or SEPHAROSE. The proteins may be oriented or non-oriented, fashioned in some orderly mode of attachment or alternatively by means of a single point attachment or flexible attachment to improve the accessibility of the binding site. Illustrative, but non-limiting means of attachment may include the use of histidine residues for immobilization of proteins on various metal-chelate supports (Ho1998); protein/autoantibody interaction (Kann2000), and avidin-biotin mediated immobilization (Patel 2000).

Alternative forms of immobilized protein devices for blood treatment contemplated for use in the instant invention include functionalized hollow fiber cartridges containing the immobilized protein therein and capable of removal of autoantibodies by adsorption from blood which is allowed to flow through the cartridges (Legallais et al. 1999). Processes for extracorporeal immunoadsorption have been disclosed for treatment of diseases such as rapidly progressive glomerulonephritis, recurrent glomerular sclerosis, systemic lupus erythematosus, cancer, myasthenia gravis, Guillain-Barré Syndrome and hemophilia.

What has not heretofore been known in the art is that a disease process which occurs behind the blood-brain barrier, such as Alzheimer's dementia, could be effectively mediated by removal, from circulating body fluids, of those autoantibodies directly associated with reduction in cognitive ability associated with the disease.

The advantages which flow from the use of biological markers as treatment targets include strengthening the effectiveness of pharmaceutical agents, and assisting in slowing down the rate of disease progression.

Accordingly, it is an objective of the instant invention to provide a process effective for delaying, reducing and/or retarding the initiation of phagocytosis of astrocytic cells, which process has been linked to loss of cognitive ability associated with the progression of Alzheimer's disease.

It is a further objective of the invention to provide a method which includes analysis of at least one body fluid of a patient to determine the presence of at least one marker indicative of Alzheimer's dementia.

It is a still further objective of the instant invention to provide an immunoassay effective for the recognition of autoantibodies linked to the progression or manifestation of Alzheimer's dementia.

It is a still further objective of the invention to provide a test kit for gauging the progression or retardation of AD comprising a non-invasive point-of-care test which can be performed utilizing a sample comprising blood or any blood product.

It is yet a still further objective of the instant invention to provide a process and a related device effective for the selective removal of at least one antibody linked to the progression and/or manifestation of Alzheimer's dementia.

Other objects and advantages of this invention will become apparent from the following description taken in conjunction with the accompanying figures wherein are set forth, by way of illustration and example, certain embodiments of this invention. The figures constitute a part of this specification and include exemplary embodiments of the present invention and illustrate various objects and features thereof.

DETAILED DESCRIPTION OF THE INVENTION

The markers which are targeted according to the method of the invention are those which are released into the circulation as a consequence of disease state and may be present in the blood or in any blood product, for example plasma, serum, cytolyzed blood, e.g. by treatment with hypotonic buffer or detergents and dilutions and preparations thereof, and other body fluids, e.g. CSF, saliva, urine, lymph, and the like.

For some markers, detectable levels of the marker are present normally in an individual. However, in response to a variety of physical, chemical, and etiologic insults such as brain injury, or disease, i.e. Alzheimer's, epilepsy, and multiple sclerosis, these levels become elevated due to a modification of stimulation, ultimately causing neuronal dysfunction and death.

Western Blotting

Figure 1:
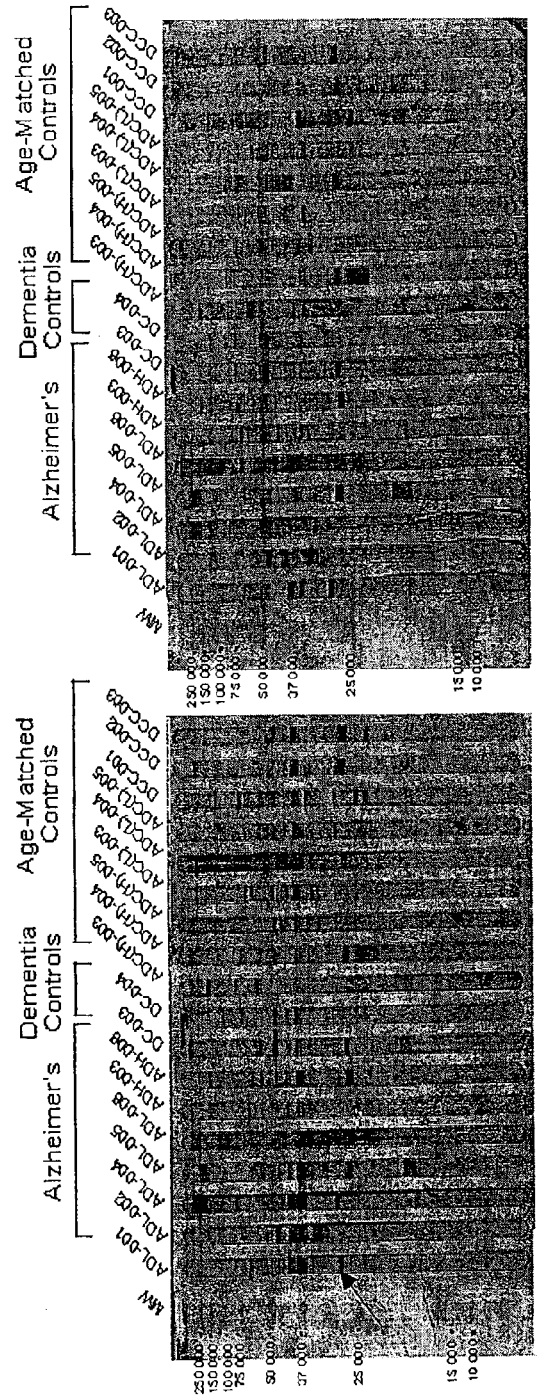
FIG. 1 is of Western blots of brain tissue extracts comparing proteins found in AD brain to normal brain.

With reference to FIG. 1, tissue samples are obtained postmortem and are stored frozen until use. For experimental preparation, tissue samples are thawed and minced with a scalpel and subsequently transferred to glass tubes. A solution of phosphate buffered saline (PBS)containing a protease inhibitor cocktail, is added to the minced tissue, then homogenized using a polytron homogenizer. A detergent (TRITON X100) is added to the homogenization buffer to enhance the extraction of proteins that are normally associated with cell membranes. The crude homogenate is centrifuged at 10,000 RPM in a refrigerated super-speed centrifuge to remove unbroken cells and cell debris which form a pellet. The pellet is extracted two more times by resuspending the pellet in the homogenization buffer and centrifugation as described above. The tissue extract containing the proteins is further subjected to electrophoresis on a polyacrylamide gel (12.5%) containing SDS and DTT to denature all the proteins. Following electrophoresis, the proteins are transferred onto a membrane (PVDF), blocked overnight with a 5% Blotto/50 mM Tris Buffered Saline (TBS) pH 7.4 at 4° C. and incubated with serum from patients diagnosed with Alzheimer's disease for a period of 1 hour. After this incubation, the membrane is washed with TBS containing 0.05% TWEEN 20 (TTBS); and a solution containing the secondary antibody (goat anti-human IgG) conjugated to alkaline phosphate is added and incubated for an additional 2 hours. Following this incubation, the membrane is washed and the substrate (BioRad's alkaline phosphate substrate kit) is added which initiates the reaction for color development. Rinsing with ultra pure water terminates the reaction. The membrane is allowed to air dry, then is photographed. The photograph is then analyzed using specialized software to identify the protein bands that are present.

2D-gel Electrophoresis

Figure 2:
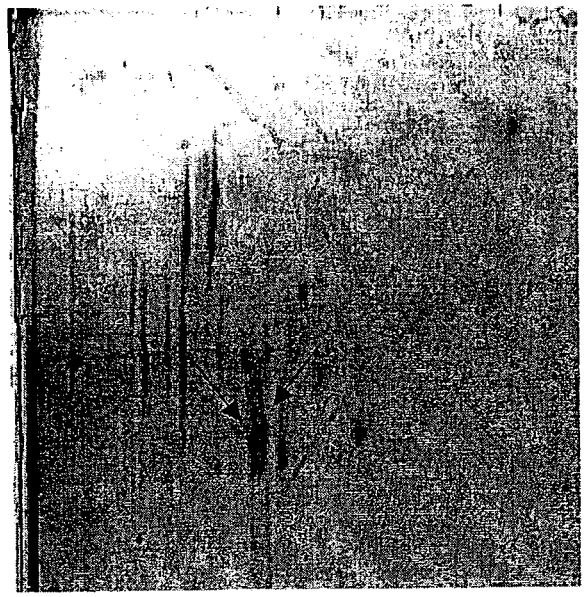
FIG. 2 is of 2D gels of brain extract from FIG. 1 highlighting the proteins of interest found in AD brain only.
Figure 2:

With reference to FIG. 2, brain tissue extracts are separated by isoelectric focusing (IEF) using the Novex IEF gel system (pH gradient 3–10) for the first dimension. Proteins are further separated by SDS-PAGE (12.5% acrylamide) for the second dimension. Gels are then stained using Coomassie Blue stain and appropriately destained to remove background. Gels are imaged using a camera connected to a computer.

Protein ID

Spots of interest are physically cut out of the gel (see arrows—FIG. 2) using a scalpel and placed in individual tubes. Gel pieces are dehydrated to remove water, making it easier for the trypsin enzyme to penetrate the gel and digest the proteins. The gel pieces are incubated overnight (16 hours) at 37° C. with the trypsin. An aliquot of the trypsin digest fluid is removed and an initial separation step is conducted using Millipore's C18 zip tips. The filtrate is then spotted onto Ciphergen's NP1 chips and peptide sequencing is conducted. A trypsin blank is included on a blank piece of gel to enable a comparison of the peptide map of trypsin cleaving itself versus the protein of interest.

The sequences identified from the two spots cut out are GAPDH and GFAP; the upper band on the 2D gel (FIG. 2) corresponds to the sequence of GFAP and the lower band corresponds to GAPDH. It is apparent these bands do not appear on the normal brain extract 2D gel which would suggest these proteins play a role in the pathogenesis of AD.

The presence of antigen-presenting, HLA-DR-positive and other immunoregulatory cells, components of complement, inflammatory cytokines and acute phase reactants have been established in tissue of AD neuropathology. Although the data do not confirm the immune response as a primary cause of AD, they indicate involvement of immune processes at least as a secondary or tertiary reaction to the preexisting pathogen and point out its driving-force role in AD pathogenesis (Popovic et al., Int. J. Neurosci., 95, 3–4, (1998)).

In a further contemplated embodiment of the invention, a method of immune system modulation can be employed utilizing a patient's own immune system to specifically target autoantibodies of interest associated with AD to be attacked and eliminated. It has long been known in the prior art to incorporate an individual's own T-lymphocyte cells to kill tumor cells. Only recently has this type of therapy demonstrated success. By focusing on proteins particularly expressed by the biochemical markers of interest, antigen-presenting cells with this protein particularly expressed on its surface can bind to CD28 on the T-cell surface to then induce the cascade of events, ultimately eliminating cells expressing the protein particularly expressed. In current strategies, single chain antibodies are fused to the said protein particularly expressed by a cell type of interest assisting in the T-cell activation process.

Confocal Microscopy

EXPERIMENT #1

CCF-STTG1 cells (brain astrocytes that are GFAP +ve) are co-cultured with RAW cells (macrophage cell line) in the presence of, or without mouse anti-GFAP antibodies. Astrocytes are incubated with anti-GFAP Ab for 10 minutes and then the macrophages are added after and left to incubate for 30 min.

Results:

Without the Ab, the macrophages are not associated with the astrocytes, but in the presence of anti-GFAP antibodies the macrophages are clumped around the astrocytes. This initiates the phagocytosis process.

EXPERIMENT #2

CCF-STTG1 cells (brain astrocytes that are GFAP +ve) are co-cultured with RAW cells (macrophage cell line) in the presence of normal serum or AD serum. Astrocytes are incubated with serum for 10 minutes and then the macrophages are added after and left to incubate for 30 min.

With normal serum, the macrophages are not associated with the astrocytes, but with AD serum the macrophages are clumped around the astrocytes. This demonstrates the start of phagocytosis and attack of the brain cells.

Figure 3:
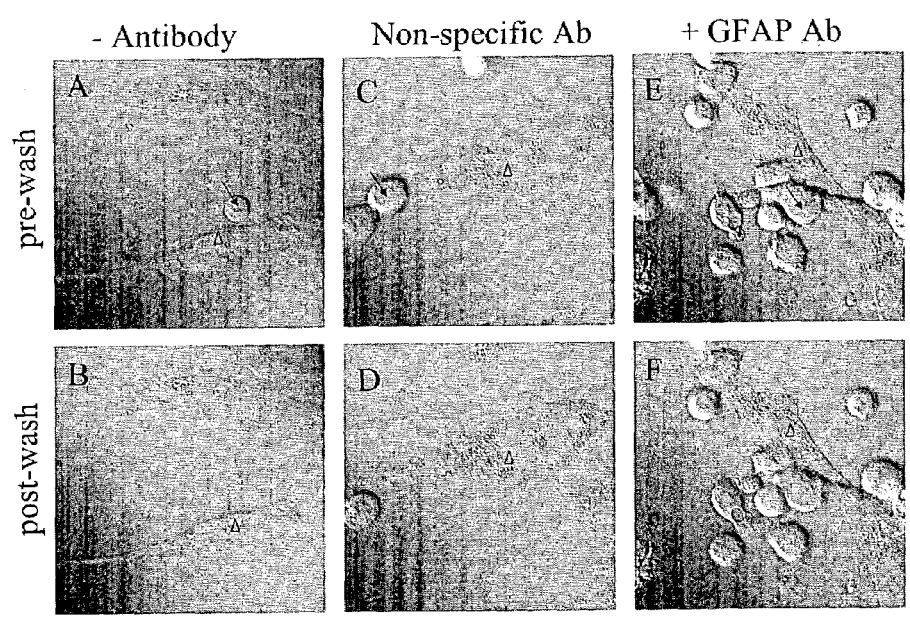
FIG. 3 is a confocal micrograph of astrocytic cell interaction with macrophage dependent upon the presence of anti-GFAP antibodies.

As seen in FIG. 3, CCF-STTG1 astrocyte cells (arrowhead) and RAW macrophages (arrows) were co-cultured in the presence of a non-specific antibodies mixture (C-D) or anti-human GFAP antibody (E-F) or absence of antibodies (A-B). Binding of macrophages to astrocytes before wash is shown in A-C-E, and interactions remaining after wash in B-D-F. Specific binding occurs only in the presence of antibody specific to GFAP protein.

Thus, removal or reduction of the concentration of antibody specific to GFAP protein will retard or eliminate the initiation of phagocytosis, and concomitantly retard or eliminate the initiation of Alzheimer's related changes in the brain.

The level of any one or all of the specific markers of interest found in the patient's body fluid may be used for purposes of monitoring removal efficiency. Body fluid samples may be taken from a patient at one point in time or at different points in time for ongoing analysis. Typically, first sample is taken from a patient upon presentation with possible symptoms of AD and analyzed for presence of the particular markers. By "sample" is meant a body fluid such as blood. All the markers can be measured with one assay device or by using a separate assay device for each marker in which case aliquots of the same sample can be used. It is preferred to measure each of the markers in the same single sample, irrespective of whether the analyses are carried out in a single analytical device or in separate devices so that the level of each marker simultaneously present in a single sample can be used to provide meaningful data.

The presence of each marker is determined using antibodies specific for each of the markers and detecting specific binding of each antibody to its respective marker. Any suitable direct or indirect assay method may be used, including those which are commercially available to determine the level of each of the specific markers measured according to the invention. The assays may be competitive assays, sandwich assays, and the label may be selected from the group of well-known labels such as radioimmunoassay, fluorescent or chemiluminescence immunoassay, or immunoPCR technology. Extensive discussion of the known immunoassay techniques is not required here since these are known to those of skilled in the art. See Takahashi et al. (Clin Chem 1999;45(8):1307) for S100B assay.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

One skilled in the art will readily appreciate that the present invention is well adapted to carry out the objects and obtain the ends and advantages mentioned, as well as those inherent therein. The oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for retarding phagocytosis of astrocytic cells comprising:
   determining the presence in body fluid of autoantibodies against glial fibrillary acidic protein (GFAP); and
   removing said autoantibodies from said body fluid whereby said removing retards phagocytosis of astrocytic cells.

* * * * *